United States Patent [19]

Mitzlaff et al.

[11] 4,149,941
[45] Apr. 17, 1979

[54] PROCESS FOR PREPARING FUNGICIDAL MONOALKOXY AND DIALKOXY N-SUBSTITUTED CYCLIC AMINES

[75] Inventors: Michael Mitzlaff, Bad Homburg; Klaus Warning, Liederbach; Harald Jensen, Frankfurt, all of Fed. Rep. of Germany

[73] Assignee: Hoechst Aktiengesellschaft, Frankfurt, Fed. Rep. of Germany

[21] Appl. No.: 915,766

[22] Filed: Jun. 15, 1978

Related U.S. Application Data

[62] Division of Ser. No. 720,384, Sep. 3, 1976, Pat. No. 4,118,500.

[30] Foreign Application Priority Data

Sep. 6, 1975 [DE] Fed. Rep. of Germany ....... 2539777
Dec. 22, 1975 [DE] Fed. Rep. of Germany ....... 2557790
Jul. 29, 1976 [DE] Fed. Rep. of Germany ....... 2634049

[51] Int. Cl.$^2$ .............................................. C25B 3/10
[52] U.S. Cl. .................................... 204/59 R; 204/72; 204/78
[58] Field of Search ........................... 204/59 R, 72, 78

[56] References Cited

U.S. PATENT DOCUMENTS

| | | | |
|---|---|---|---|
| 3,459,643 | 8/1969 | Ross et al. ......................... | 204/59 R |
| 3,941,666 | 3/1976 | Mitzlaff et al. ..................... | 204/79 |
| 4,036,712 | 7/1977 | Mitzlaff ............................... | 204/59 R |

OTHER PUBLICATIONS

Mizuno, J. Electrochem. Soc. Japan, 29 (2) E112-E114 (1961).
Shono et al., J. Amer. Chem. Soc., 97 (15) 4264-4268, 7/75.

Primary Examiner—F. C. Edmundson
Attorney, Agent, or Firm—Curtis, Morris & Safford

[57] ABSTRACT

Novel alkoxy derivatives of N-substituted cyclic amines of the formula

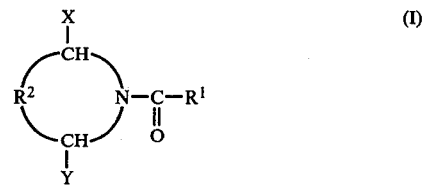

where
R$^1$ is hydrogen, an alkyl group having from 1 to 8 carbon atoms, an aryl group having from 6 to 10 carbon atoms, an alkoxy group having from 1 to 4 carbon atoms, an aralkoxy or aroxy group,
R$^2$ is a linear or branched alkylene group having from 1 to 4 carbon atoms in the chain,
X is OR$^3$, where R$^3$ represents an alkyl group having from 1 to 4 carbon atoms,
Y is hydrogen, (C$_1$-C$_4$)-alkyl, (C$_1$-C$_4$)-O-alkyl, provided that in the case where R$^1$ is an alkoxy group having from 1 to 4 carbon atoms, Y is not H.

6 Claims, 1 Drawing Figure

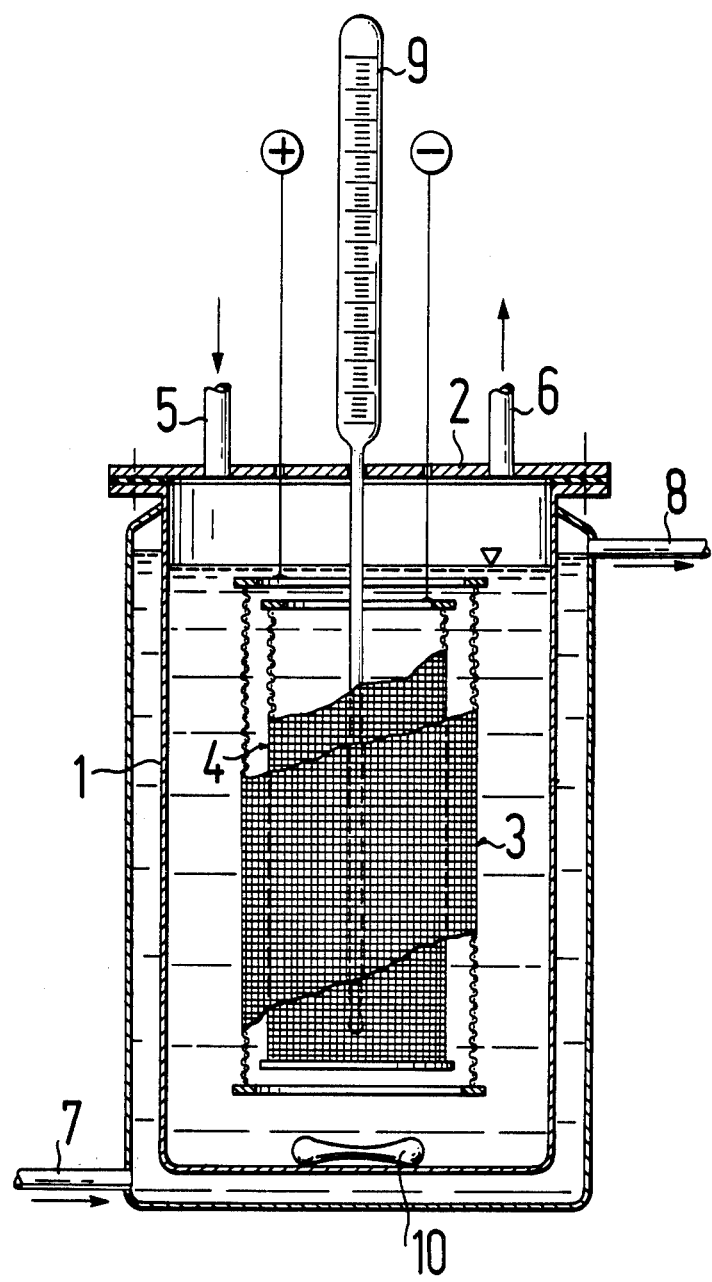

PROCESS FOR PREPARING FUNGICIDAL MONOALKOXY AND DIALKOXY N-SUBSTITUTED CYCLIC AMINES

This is a division of application Ser. No. 720,384 filed Sept. 3, 1976; now U.S. Pat. No. 4,118,500.

It is known that carboxylic acid amides alkylated at the nitrogen atom are electrochemically converted to N-α-alkoxy-alkyl-carboxylic acid amides (see German Offenlegungsschrift No. 2,113,338). In this process, the N-alkylated carboxylic acid amides are electrolyzed at a temperature of up to about 100° C. in an alcohol excess in the presence of conducting salts, for example alkali metal or tetraalkylammonium-tetrafluoroborates, -hexafluorophosphates or -nitrates. The electrolysis cell may contain a stationary or streaming electrolyte, and the current quantities do not exceed 2.4 Faraday per mol of carboxylic acid amide.

German Offenlegungsschrift No. 2,503,114 proposes to electrolyze special starting materials indicated in German Offenlegungsschrift No. 2,113,338 in the presence of certain determined conducting salts to form the corresponding N-α-alkoxyalkylcarboxylic acid amides, while optionally using larger current quantities. This results in an increased yield of substance, and the reaction batch can be worked up more easily.

However, only such N-alkylcarboxylic acid amides have been used as starting materials, in which the alkyl radicals located at the nitrogen atom were not linked with each other in the form of a ring.

On the other hand, it is also known that N-alkylcarboxylic acid amide derivatives, that is, N-alkylcarbamic acid esters the alkyl radicals located at the nitrogen atom of which form a closed ring with each other may be electrochemically alkoxylated to form the N-α-alkoxy derivatives (J. Am. Chem. Soc. 97 (1975), pp. 4264–4268). In detail, this paper deals with the electrolysis of N-carbomethoxypyrrolidine and N-carbomethoxypiperidine in methanolic solution with the use of tetraethylammonium tosylate (= tetraethylammonium salt of p-toluenesulfonic acid), in which process the monomethoxylated compounds (α-methoxy-N-carbomethoxypyrrolidine or α-methoxy-N-carbomethoxypiperidine) are obtained with product yields of 65 and 72%, respectively.

In accordance with the present invention, and in order to improve and develop the known electrochemical alkoxylation reactions, N-alkylcarboxylic acid amides and N-alkylcarbamic acid esters the alkyl radicals located at the nitrogen atom of which form a ring are subjected to the electrolysis conditions of German Offenlegungsschriften Nos. 2,113,338 and 2,503,114. The starting compounds are hereinafter defined also as N-substituted cyclic amines. Thus, a novel class of compounds, the alkoxy derivatives of N-substituted cyclic amines, is obtained having the formula

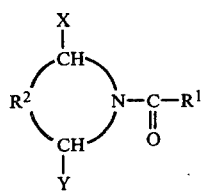

(I)

where
$R^1$ is hydrogen, an alkyl group having from 1 to 8 carbon atoms, an aryl group having from 6 to 10 carbon atoms, an alkoxy group having from 1 to 4 carbon atoms, an aralkoxy, preferably benzyloxy, group or an aryloxy, preferably phenoxy, group (these groups optionally being substituted, preferably mono- to trisubstituted, for example by halogen, preferably F, Cl, Br, ($C_1$–$C_4$)-alkyl and/or $CF_3$), $R^2$ is a linear or branched alkylene group having from 1 to 4 carbon atoms in the chain, X is $OR^3$, where $R^3$ represents an alkyl group having from 1 to 4 carbon atoms, Y is hydrogen, ($C_1$–$C_4$)-alkyl, ($C_1$–$C_4$)-O-alkyl, or in the case where $R^1$ is an alkoxy group having from 1 to 4 carbon atoms, Y is not H.

Preferred compounds are especially those in which Y of the above formula is hydrogen, $R^1$ is hydrogen or $CH_3$, an alkyl radical having from 1 to 3 carbon atoms or optionally substituted $C_6H_5$, and $R^2$ is a linear alkylene group having from 1 to 4 carbon atoms, and furthermore those where $R^1$, X and Y each are $OCH_3$ and $R^2$ is a linear alkylene group having from 1 to 4 carbon atoms.

Examples of the new compounds are the following:

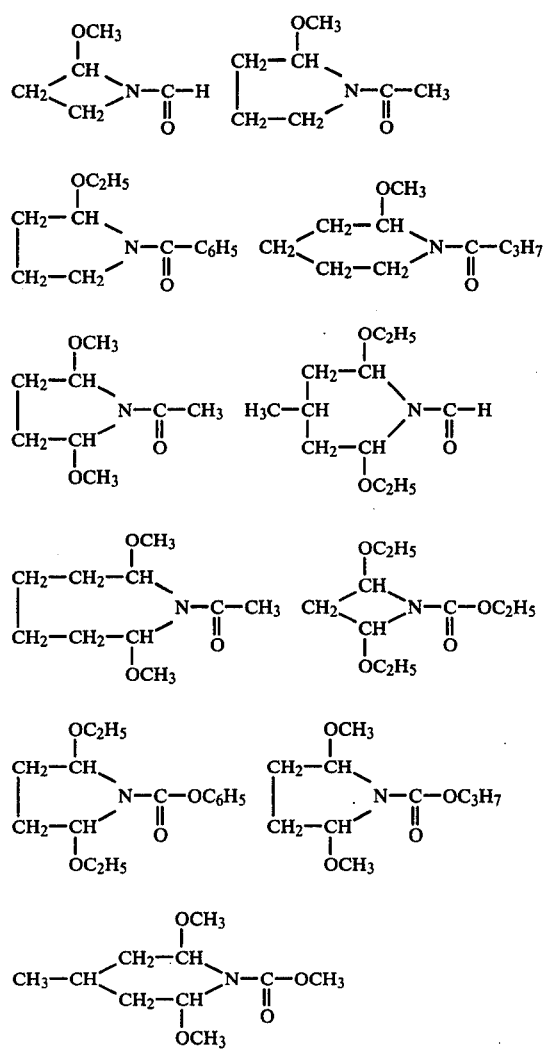

-continued

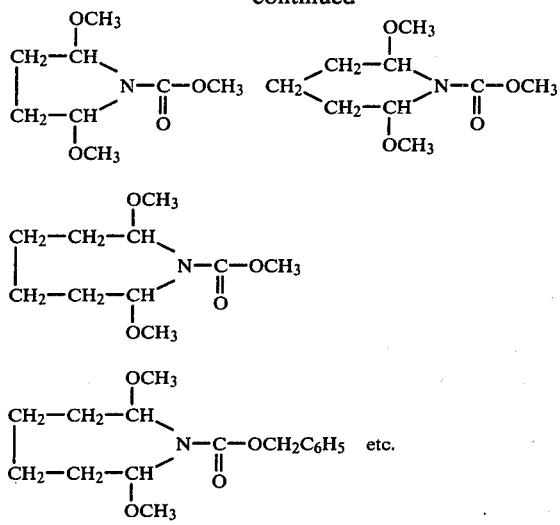

According to this invention, the novel compounds are prepared by anodic alkoxylation of carboxylic acid amide derivatives, that is, by electrolysis of the carboxylic acid amide derivatives with an alcohol of the formula $R^3OH$ ($R^3$ is an alkyl radical having from 1 to 4 carbon atoms) in the presence of at least one alkali metal (Li, Na, K, Rb, Cs) or tetra-$(C_1-C_6)$-alkyl-ammonium-tetrafluoroborate, -hexafluorophosphate and/or -nitrate as conducting salt, at a temperature of up to 100° C., in an electrolysis cell containing a stationary or streaming electrolyte; the process comprises using compounds of the formula

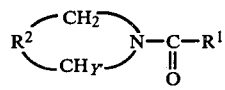  (II)

as carboxylic acid amide derivatives. The symbols $R^1$ and $R^2$ of formula II are as defined for formula I, that is:

$R^1$ is hydrogen, an alkyl group having from 1 to 8 carbon atoms, an aryl group having from 6 to 10 carbon atoms, an alkoxy group having from 1 to 4 carbon atoms, an aralkoxy (preferably the benzyloxy) group or an aroxy (preferably the phenoxy) group, and $R^2$ is a linear or branched alkylene group having from 1 to 4 carbon atoms in the chain, and Y' is H, $(C_1-C_4)$-alkyl or $(C_1-C_4)$-O-alkyl.

Examples of carboxylic acid derivatives suitable as starting substances are the following:

(a) N-acylated cyclic amines (=N-alkylcarboxylic acid amides the N-alkyl radicals of which form a closed ring): N-formyl-azetidine, N-acetyl-azetidine, N-propionyl-azetidine, N-butyryl-azetidine, N-benzoyl-azetidine, N-formylpyrrolidine, N-acetylpyrrolidine, N-propionylpyrrolidine, N-butyrylpyrrolidine, N-benzoylpyrrolidine, N-formylpiperidine, N-acetylpiperidine, N-propionylpiperidine, N-butyrylpiperidine, N-benzoylpiperidine, N-formylhexahydroazepine, N-acetylhexahydroazepine, N-propionylhexahydroazepine, N-benzoylhexahydroazepine etc.. Optionally, also those cyclic N-acylamines may be used as starting compounds which are substituted in one α-position by lower alkyl groups (preferably $C_1-C_4$, especially $CH_3$), for example 1-formyl-2,2-dimethylazetidine, 1-benzoyl-2-methylpiperidine, provided that at least one α-position remains unsubstituted.

(b) N-carboalkoxylated, N-carboaralkoxylated and N-carbophenoxylated cyclic amines (=N-alkylcarbamic acid esters the N-alkyl groups of which form a closed ring): N-carbomethoxypyrrolidine, N-carboethoxypyrrolidine, N-carbo-n-propoxypyrrolidine, N-carbo-n-butoxypyrrolidine, N-carbo-i-butoxypyrrolidine, N-carbomethoxypiperidine, N-carboethoxypiperidine, N-carbo-i-propoxypiperidine, N-carbo-n-butoxypiperidine, N-carbophenoxypiperidine, N-carbobenzyloxypiperidine, N-carbomethoxyhexahydroazepine, N-carboethoxyhexahydroazepine, N-carbo-n-butoxyhexahydroazepine etc..

Preferred starting compounds are those substances of formula (II) where $R^1$ is hydrogen, an alkyl group having from 1 to 3 carbon atoms, or an optionally substituted $C_6H_5$ group, and $R^2$ is a linear alkylene group having from 1 to 4 carbon atoms, especially N-formyl- and N-acetyl-pyrrolidine, N-formyl- and N-acetyl-piperidine and N-carbomethoxypyrrolidine and -piperidine.

The starting compounds are prepared in a simple manner, for example by reaction of the corresponding cyclic amines with acid chlorides or chloroformic acid esters according to known methods. An example for the reaction of cyclic amines with chloroformic acid esters is that of piperidine with chloroformic acid methyl ester in the presence of KOH (C. Schotten, Ber. Deutsch. Chem. Ges. 16, 643 (1883)), which yields N-methoxycarbonylpiperidine.

Suitable alcohols $R^3OH$ are methanol, ethanol, n-propanol, isopropanol, n-butanol, sec.-butanol etc.; methanol and ethanol being preferred, especially methanol.

Conducting salts used for the process of the invention are alkali metal and tetraalkylammonium-tetrafluoroborates, -hexafluorophosphates and -nitrates. Several of these conducting salts may also be used simultaneously. The alkyl radicals present in the tetraalkylammonium group are those having from 1 to 6, preferably from 1 to 4 carbon atoms, especially the methyl and ethyl groups. Examples are the following conducting salts: $LiBF_4$, $NaBF_4$, $KBF_4$, $NaPF_6$, $KPF_6$, $RbPF_6$, $NaNO_3$, tetramethylammonium-tetrafluoroborate, tetraethylammonium-tetrafluoroborate, tetra-n-butylammonium-tetrafluoroborate, tetraethylammonium-hexafluorophosphate, tetra-n-propylammonium-hexafluorophosphate, tetra-n-butylammonium-hexafluorophosphate, tetramethylammonium-nitrate etc.. Preferred conducting salts are the sodium and potassium salts of tetrafluoroboric or hexafluorophosphoric acid, or the tetraalkylammonium salts of tetrafluoroboric acid, especially tetramethylammonium-tetrafluoroborate.

The concentration of conducting salt in the electrolysis solution should be from about 0.01 to about 2 mols/liter, preferably from about 0.02 to 1.0 mol/l. The suitable electrolysis temperature range is from about $-10°$ to $+100°$ C., preferably from about 0° to 60° C.

In the electrolysis solution, a molar ratio of starting acid amide to alcohol of from about 1:1 to about 1:100 may be chosen; a molar ratio of from about 1:2 to about 1:60, especially from about 1:5 to about 1:50 being preferred.

Depending on the current quantities applied in the process of the invention, mono- or, if both α-positions are free, dialkoxylated final products are obtained. Monoalkoxylated compounds are obtained with high yields when the current quantity applied does not exceed 2 to 2.5 Faraday per mol of starting acid amide. At a current quantity of more than 4 Faraday, preferably from about 4 to 5 Faraday per mol of starting compound where Y' is H, those compounds of formula I where X and Y are alkoxy radicals are formed in most cases. At current quantities between the two indicated ranges, mixtures of mono- and dialkoxylated cyclic amine compounds are obtained. The mono- and dialkoxylated amine compounds are novel substances except those where $R^1$ of formula (I) is alkoxy and simultaneously Y is H.

The electrochemical alkoxylation according to the present invention may be carried out batchwise or continuously.

Batchwise electrolysis may be carried out for example in an electrolysis cell as shown in the accompanying drawing.

Referring now to this drawing, the electrolysis cell (1) is provided with a tightly closing cover plate (2) through which the current supply ducts for the electrodes (3) and (4) are passed, and in which cover plate there are openings for the feed of the electrolysis solution (5), for the off-gas (6) and for a thermometer (9). The orifice for the off-gas may be provided with a reflux condenser where vaporized amounts of the electrolysis mixture may be recondensed. The electrolysis cell has a jacket which can be connected to a heating or liquid cooling cycle via inlet (7) and outlet (8). The temperature of the electrolysis solution is controlled by means of a thermometer (9) or a thermocouple. The two electrodes, anode (3) and cathode (4) are arranged at a distance from each other of from 0.5 to 50 mm, preferably from 1 to 15 mm.

As electrode material, nets or plates of palladium or platinum, or metal electrodes coated with noble metals, preferably titanium electrodes are used as cathodes, while the anodes are metal electrodes coated with mixed oxides, preferably titanium anodes, or slotted or unslotted graphite plates. A net-like design of the anodes is particularly advantageous, since hydrogen gas formed during the electrolysis may be more easily discharged therefrom and the gas current thus generated ensures additionally a homogeneous intermixing of the electrolysis solution. The vertical position of the electrodes is not compulsory, it may as well be horizontal. It is also possible to use several electrode pairs, as this has proved to be advantageous in a block-like combination of angular or straight capillary gap electrodes with or without vibration of the electrodes. The solution is thoroughly mixed during the electrolysis, especially in the case of the block-like combinations, by means of, preferably, an agitator, for example a magnetic agitator (10), or by pump circulation.

The use of flow cells with packed bed electrodes of bipolar circuit in mixtures of conducting and non-conducting particles of identical grain in a 1:2 to 1:4 ratio, the conducting particles consisting of the cited electrode material (except the titanium particles coated with mixed oxides), preferably of graphite, is advantageous in the case of streaming electrolytes, since this increases the space-time yield. When flow cells with "layer bed" electrodes are used, the layers being composed of conducting particles of identical grain consisting of the cited electrode material (except titanium particles coated with mixed oxides), preferably of graphite, which layers are separated by thin porous non-conducting inorganic or organic materials in the form of plates, fabrics, nets, felts or fleeces, for example a glass fiber fleece or polypropylene wire mesh, in such a manner that these materials are in vertical or parallel position to the lines of electric field, still better energy and space-time yields are obtained.

When the process is carried out continuously, the cover plate (2) of the electrolysis vessel (1) is provided with a further opening for continuous pump circulation of the electrolysis solution. Part of the pump-circulated electrolysis solution is separated in order to work up the product. After having examined the electrolysis solution with respect to the ratio of intended reaction product to starting material by means of nuclear resonance spectroscopy or chromatography methods, the solution is worked up in known manner. After having been adjusted to the required molar ratio, the starting compounds recovered in the distillation are recycled into the pump-circulated electrolysis solution, together with the necessary amount of a conducting salt-forming agent.

Generally, the electrolysis is carried out under normal pressure, but reduced pressure may also be applied. In order to prevent the formation of explosive gas mixtures of hydrogen and air, it is advantageous to operate with the addition of an inert gas such as nitrogen.

The conducting salt is added after having prepared the alcoholic solution. However, the sequence may be altered.

It is not required to exclude water from the electrolysis by all means, since small moisture amounts do not disturb the course of the reaction according to the present invention.

The process can be optimized in view of energy and product yield by a very high conversion rate of the cyclic carboxylic acid amide derivative (II) of, for example, more than 99%, which moreover is very advantageous for the work-up of the electrolysis solution. Thus, electrolysis is generally continued until practically all starting material is converted, so that its subsequent separation from the reaction product is no longer necessary.

After having fed in the required current quantity, the electrolysis current is switched off, the discharged electrolysis product is liberated from the conducting salt and worked up in known manner, preferably by distillation. The reaction product of the electrolysis may be examined for purity according to, for example, a nuclear resonance spectroscopy method.

The current density is adjusted to about 1 to 50 A/dm$^2$, preferably 2 to 30 A/dm$^2$. A lower current density, although possible, retards the formation of product.

When tetraethylammonium tosylate known from J. Am. Chem. Soc. 97 (1975), pp. 4264–4268 is used as conducting salt for the electrochemical alkoxylation of N-carbomethoxypyrrolidine or N-carbomethoxypiperidine to the corresponding α-methoxy derivatives instead of employing the conducting salts in accordance with this invention for the electrochemical alkoxylation of the carboxylic acid amide derivatives (II), there are obtained considerably decreased yields of the intended alkoxy derivative as compared to the process of the invention. Moreover, at a current throughput of 2.0 Faraday/mol of N-acylated cyclic amine (II) as starting material, the amine is only insufficiently converted when tetraethylammonium tosylate is used as conducting salt, and the converted proportion contains already a considerably amount of the α,α'-dialkoxylated product. The special nature of the conducting salts therefore is of decisive and critical importance in the electrochemical alkoxylation of the N-acylated amines.

The α-alkoxy derivatives of N-acylated, N-carboalkoxylated, N-carboaralkoxylated and N-aroxylated cyclic amines obtained according to the electrochemical process of this invention generally in the form of colorless liquids vacuum-distillable without decomposition are interesting intermediate products especially for the preparation of α,ω-diaminocarboxylic acids, for example via the reaction with HCN, NH₃ and optionally CO₂, and hydrolysis of the aminonitrile or hydantoin formed. Thus, for example, N-acyl-, N-carboalkoxy-, N-carboaralkoxy- and N-carboaroxy-α-alkoxy-piperidine are starting compounds for a simple lysine synthesis, and N-acyl-, N-carboalkoxy-, N-carboaralkoxy- and N-carboaroxy-α-alkoxy-pyrrolidine are starting substances for an ornithine synthesis.

Synthesis of α,ω-diaminocarboxylic acids starts from monoalkoxylated N-substituted cyclic amines of the formula

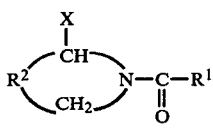

where R¹, R² and X are as defined for formula I. The starting compounds are reacted with at least equimolar amounts of HCN and NH₃ and optionally CO₂ in an aqueous or aqueous-alcoholic reaction medium, in a temperature range of from about 70° to 150° C., preferably from 90° to 120° C., and under substantially autogenic pressure. The reaction product obtained, aminonitrile in the case of reaction with HCN and NH₃, and hydantoin in the case of reaction with HCN, NH₃ and CO₂, is saponified in known manner. The corresponding reaction schemes are the following:

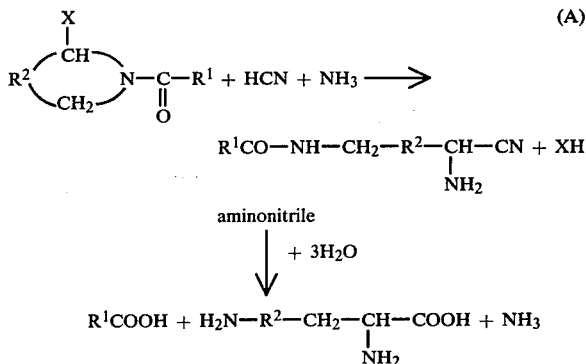

or, when CO₂ is concomittantly used,

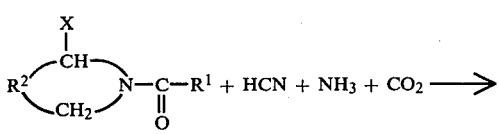

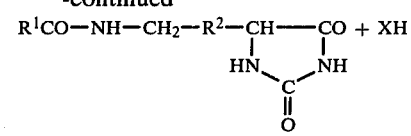

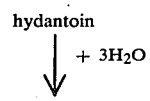

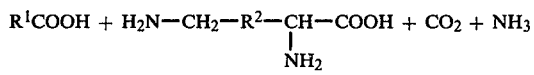

Furthermore, the compounds of formula I in accordance with this invention are interesting intermediate products for the preparation of trimeric Δ¹-piperidines and of trimeric 1-pyrroline in the case where R¹ is a linear or branched C₁-C₄-alkyl radical and Y is H.

In this case the acyl radical may be split off the nitrogen (R¹—CO—) by acidic or alkaline means; the deacylated nitrogen heterocycle splitting off alcohol (R²OH) in an alkaline medium and being converted to a cyclic nitrogen base having a C=N double bond, which subsequently trimerizes in known manner. The reaction proceeds for example according to the following scheme:

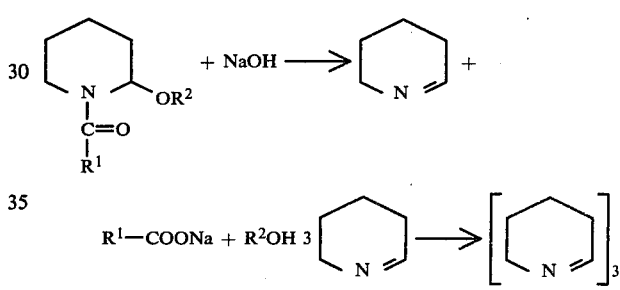

The trimers of Δ¹-piperidine and of 1-pyrroline, for their part, are interesting intermediate products in the synthesis of numerous products of technical importance. Thus, for example, the reaction of trimeric Δ¹-piperidine or 1-pyrroline with phenylmethylketones in the presence of magnesium methylcarbonate, as described in German Offenlegungsschrift No. 2,418,480, yields 2-aza-cycloalkylmethyl substituted phenylketones having an anticoagulation effect. The hitherto known methods for the preparation of tripiperidine and 1-pyrroline give only poor yields and can be used only on a laboratory scale because of the necessary use of dangerous substances, for example perchlorylfluoride (D. M. Gardner et al., J. Org. Chem. 32, 1115 (1967)), N-chloropiperidine or N-chloropyrrolidine (C. Schopf et al., Liebigs Ann. Chem. 559, 1 (1948); D. W. Fuhlhage and C. A. Van der Werf. J. Am. Chem. Soc. 80, 6249 (1958)).

The alkoxy derivatives of the invention may be used for the manufacture of pharmaceuticals and plant protecting products. Furthermore, they are excellent plant protecting agents per se. Preferred are the monoalkoxylated derivatives benzoylated at the nitrogen atom. Formulation additives and inert materials may of course be present.

The following examples illustrate the invention. The following Comparative Example, wherein the conducting salt according to J. Am. Chem. Soc. 97 (1975), 4264–4268 is used, precedes the examples in accordance with this invention.

In an electrolysis cell made of glass and having a capacity of about 400 ml, 96.0 g of 1-acetylpiperidine and 241.8 g of methanol are electrolyzed in the presence of 22.75 g of tetraethylammonium tosylate (tosylate = salt of p-toluenesulfonic acid) as conducting salt. Two concentrically arranged platinum network cylinders having 225 meshes per cm$^2$ and diameters of 15 and 30 mm and a height of 100 mm are immersed in the solution. The exterior electrode is connected as anode. The temperature is maintained at about 10° C. during the electrolysis. After having switched on the electrolysis DC the anode current density is 3 A/dm$^2$. After the throughput of a current quantity of 2.0 Faraday per mol of 1-acetylpiperidine, the current is switched off. The mean cell voltage calculated is 7.5 volts.

After the work-up by means of molecular distillation, a mixture is obtained which according to a NMR analysis is composed as follows: 63.4 g of 1-acetyl-2-methoxypiperidine, 14.6 g of 1-acetyl-2,6-dimethoxypiperidine and 20.4 g of 1-acetylpiperidine. This corresponds to a product yield of 53.4% of 1-acetyl-2-methoxypiperidine and to a current efficiency of 53.4%.

EXAMPLE 1

A mixture of 169.8 g of N-formylpiperidine and 495.3 g of methanol containing 2.41 g of tetramethylammonium tetrafluoroborate as conducting salt in dissolved state is charged to an electrolysis cell corresponding to the accompanying drawing and having a capacity of 1000 ml, provided with cover and reflux condenser. Two concentrically arranged platinum network cylinders having 225 meshes per cm$^2$ and diameters of 24 and 36 mm at a height of 95 mm are immersed as electrodes in the solution, the exterior electrode serving as anode. The temperature is maintained at about 20° C. during the electrolysis. After having switched on the electrolysis DC the anode current density is 3 A/dm$^2$. After a throughput of 2.0 Faraday per mol of N-formylpiperidine the current is switched off. The calculated mean cell voltage is 21.7 volts.

After work-up of the electrolysis solution in known manner, 199.6 g of 1-formyl-2-methoxypiperidine (boiling point 50° C./0.13 mbar; $n_D^{25}=1.4718$) are obtained, which corresponds to a product yield of 92.9% and a current efficiency of 92.9%.

EXAMPLE 2

In the same manner as indicated in Example 1, there are electrolyzed 113.3 g of N-formylpiperidine and 320.0 g of methanol in the presence of 1.61 g of tetramethylammonium tetrafluoroborate as conducting salt. In this case, however, the current is switched off after the throughput of a current quantity of 7.6 Faraday per mol of N-formylpiperidine. The calculated mean cell voltage is 22.4 volts.

Work-up of the electrolysis solution gives 150.1 g of 1-formyl-2,6-dimethoxypiperidine (boiling point 74° C./0.1 mbar; $n_D^{25}=1.4721$), which corresponds to a product yield of 86.6% and a current efficiency of 45.6%.

EXAMPLE 3

In the same manner as indicated in Example 1, there are electrolyzed 190.8 g of N-acetylpiperidine and 480.7 g of methanol in the presence of 3.34 g of tetramethylammonium tetrafluoroborate as conducting salt. After the throughput of a current quantity of 2.0 Faraday per mol of N-acetylpiperidine the current is switched off. The calculated mean cell voltage is 28.9 volts.

Work-up of the electrolysis solution gives 217.4 g of 1-acetyl-2-methoxypiperidine (boiling point 53° C./0.13 mbar; $n_D^{25}=1.4700$), which corresponds to a product yield of 92.2% and a current efficiency of 92.2%. According to the comparative example, a yield of 1-acetyl-2-methoxypiperidine of only 54.4% was obtained from the same starting compounds, but with tetraethylammonium tosylate as conducting salt.

EXAMPLE 4

In the same manner as indicated in Example 1, there are electrolyzed 186.6 g of N-benzoylpiperidine and 316.0 g of methanol in the presence of 1.59 g of tetramethylammonium tetrafluoroborate as conducting salt. The current, however, is switched off in this case after the throughput of a current quantity of 2.0 Faraday per mol of N-benzoylpiperidine. The calculated mean cell voltage is 28.7 volts.

Work-up of the electrolysis solution gives 185.1 g of 1-benzoyl-2-methoxypiperidine (boiling point 98° C./0.5 mbar; $n_D^{25}=1.5368$), which corresponds to a product yield of 85.6% and a current efficiency of 70.8%.

EXAMPLE 5

In the same manner as indicated in Example 1, there are electrolyzed 28.4 g of N-benzoylpiperidine and 48.1 g of methanol in the presence of 0.24 g of tetramethylammonium tetrafluoroborate as conducting salt.

The contents of the cell, however, are about 80 ml, the electrodes have diameters of 15 and 30 mm at 50 mm of height. Only after the throughput of 4.0 Faraday per mol of N-benzoylpiperidine the current is switched off. The calculated mean cell voltage is 58.7 volts.

Work-up of the electrolysis solution gives 23.4 g of 1-benzoyl-2,6-dimethoxypiperidine (boiling point 57° C./0.3 mbar; $n_D^{25}=1.5332$), which corresponds to a product yield of 71.2% and a current efficiency of 71.2%.

EXAMPLE 6

In the same manner as indicated in Example 5 there are electrolyzed 17.7 g of N-formylpyrrolidine and 57.2 g of methanol in the presence of 0.29 g of tetramethylammonium tetrafluoroborate as conducting salt. In this case, however, the current is switched off after the throughput of already 2.0 Faraday per mol of N-formylpyrrolidine. The calculated mean cell voltage is 28.8 volts. Work-up of the electrolysis solution gives 20.0 g of 1-formyl-2-methoxypyrrolidine (boiling point 39°–40° C./0.1 mbar; $n_D^{25}=1.4700$), which corresponds to a product yield of 86.6% and a current efficiency of 86.6%.

EXAMPLE 7

In the same manner as indicated in Example 6 there are electrolyzed 19.6 g of N-acetylpyrrolidine and 55.6 of methanol in the presence of 0.28 g of tetramethylammonium tetrafluoroborate as conducting salt. After throughput of 2.0 Faraday per mol of N-acetylpyrrolidine the current is switched off. The calculated mean cell voltage is 32.7 volts. Work-up of the electrolysis solution gives 19.9 g of 1-acetyl-2-methoxypyrrolidine (boiling point 53° C./0.1 mbar; $n_D^{25}=1.4674$), which corresponds to a product yield of 80.0% and a current efficiency of 80.0%.

EXAMPLE 8

In the same manner as indicated in Example 6 there are electrolyzed 8.5 g of N-acetylpiperidine and 49.7 g of n-butanol in the presence of 0.3 g of tetramethylammonium tetrafluoroborate as conducting salt. After throughput of 2.5 Faraday per mol of N-acetylpiperidine the current is switched off. The calculated mean cell voltage is 91 volts. Work-up of the electrolysis solution gives 7.6 g of 1-acetyl-2-n-butoxypiperidine (boiling point 70° C./0.1 mbar; $n_D^{25}=1.4656$), which corresponds to a product yield of 56.8% and a current efficiency of 45.5%.

EXAMPLE 9

In the same manner as indicated in Example 6 there are electrolyzed 23.2 g of N-acetylhexahydroazepine and 57.7 g of methanol in the presence of 0.26 g of tetramethylammonium tetrafluoroborate as conducting salt. After throughput of 2.5 Faraday per mol of N-acetylhexahydroazepine the current is switched off. The calculated mean cell voltage is 40.8 volts. Work-up of the electrolysis solution gives 25.4 g of 1-acetyl-2-methoxyhexahydroazepine (boiling point 53° C./0.06 mbar; $n_D^{25}=1.4775$), which corresponds to a product yield of 90.1% and a current efficiency of 71.5%.

EXAMPLE 10

In the same manner as indicated in Example 6 there are electrolyzed 19.3 g of 1-formyl-2,2-dimethylazetidine and 54.7 g of methanol in the presence of 0.27 g of tetramethylammonium tetrafluoroborate as conducting salt. After throughput of 2.5 Faraday per mol of 1-formyl-2,2-dimethoxyazetidine the current is switched off. The calculated mean cell voltage is 32.6 volts. Work-up of the electrolysis solution gives 12.2 g of 1-formyl-4-methoxy-2,2-dimethylazetidine (boiling point 52° C./0.26 mbar; $n_D^{25}=1.4496$), which corresponds to a product yield of 49.9% and a current efficiency of 39.9%.

EXAMPLE 11

In the same manner as indicated in Example 6 there are electrolyzed 21.6 g of N-acetylpiperidine and 54.4 g of methanol in the presence of 0.56 g of tetra-n-propylammonium hexafluorophosphate as conducting salt. After throughput of 2.0 Faraday per mol of N-acetylpiperidine the current is switched off. The calculated mean cell voltage is 28.7 volts. Work-up of the electrolysis solution by molecular distillation gives 21.5 g of 1-acetyl-2-methoxypiperidine, which corresponds to a product yield of 80.5% and a current efficiency of 80.5%.

EXAMPLE 12

In the same manner as indicated in Example 6 there are electrolyzed 13.1 g of N-formylpyrrolidine and 60.7 g of ethanol in the presence of 0.21 g of tetramethylammonium tetrafluoroborate as conducting salt. After throughput of 5.2 Faraday per mol of N-formylpiperidine the current is switched off. The calculated mean cell voltage is 92 volts. Work-up of the electrolysis solution gives 15.6 g of 1-formyl-2,5-diethoxypyrrolidine (boiling point 62°-64° C./0.08 mbar; $n_D^{25}=1.4565$), which corresponds to a product yield of 63.0% and a current efficiency of 50.2%.

EXAMPLE 13

In an electrolysis cell according to the Comparative Example, 96.0 g of 1-acetylpiperidine and 241.8 g of methanol are electrolyzed in the presence of 13.9 g of potassium hexafluorophosphate as conducting salt. After having switched on the electrolysis DC the anode current density is 3 A/dm². After throughput of 2.0 Faraday/mol of 1-acetylpiperidine the current is switched off. The calculated mean cell voltage is 5.6 volts. After work-up by means of molecular distillation, 105.2 g of 1-acetyl-2-methoxypiperidine (boiling point 53° C./0.13 mbar; $n_D^{25}=1.4700$) are obtained which corresponds to a product yield of 88.6% and a current efficiency of 88.6%. The product yield is only slightly lower than that of Example 3 but considerably higher than that of the Comparative Example. Furthermore, the 1-acetyl-2-methoxypiperidine is obtained selectively as in Example 3.

EXAMPLE 14

In an electrolysis cell according to the Comparative Example, 96.0 g of 1-acetylpiperidine and 241.8 g of methanol are electrolyzed in the presence of 8.22 g of sodium tetrafluoroborate as conducting salt. After having switched on the electrolysis DC the anode current density is 2 A/dm². After throughput of a current quantity of 2.0 Faraday/mol of 1-acetylpiperidine the current is switched off. The calculated mean cell voltage is 5.2 volts. After work-up by means of molecular distillation 106.9 g of 1-acetyl-2-methoxypiperidine are obtained which corresponds to a product yield of 90.1% and a current efficiency of 90.1%.

EXAMPLE 15

In an electrolysis cell according to the Comparative Example, 96.0 g of 1-acetylpiperidine and 241.8 g of methanol are electrolyzed in the presence of 8.3 g of sodium tetrafluoroborate as conducting salt. After switching on of the electrolysis DC the anode current density is 3 A/dm². After throughput of 4.0 Faraday/mol of 1-acetylpiperidine the current is switched off. The calculated mean cell voltage is 6.5 volts. After work-up by molecular distillation, 107.6 g of 1-acetyl-2,6-dimethoxypiperidine (boiling point 52° C./0.3 mbar; $n_D^{25}=1.4723$), are obtained, which corresponds to a product yield of 76.1% and a current efficiency of 76.1%.

EXAMPLE 16

In an electrolysis cell according to the Comparative Example, but having a capacity of only about 60 ml, 17.9 g of 1-acetylpiperidine and 64.8 g of ethanol are electrolyzed in the presence of 2.59 g of potassium hexafluorophosphate as conducting salt. The platinum network electrodes in this case have a height of only 50 mm. After switching on the electrolysis DC the anode current density is 1 A/dm². After throughput of 2.2 Faraday/mol of 1-acetylpiperidine the current is switched off. The calculated mean cell voltage is 42.7 volts. After work-up by molecular distillation, 17.5 g of 1-acetyl-2-ethoxypiperidine (boiling point 52° C./0.13 mbar; $n_D^{25}=1.4655$) are obtained, which corresponds to a product yield of 72.6% and a current efficiency of 66.0%.

EXAMPLE 17

In an electrolysis cell as indicated in Example 4, there are electrolyzed 19.7 g of 1-acetylpyrrolidine and 55.6 g of methanol in the presence of 0.19 g of sodium tetrafluoroborate as conducting salt. After switching on of the electrolysis DC the anode current density is 1 A/dm$^2$. After throughput of 2.0 Faraday/mol of 1-acetylpyrrolidine the current is switched off. The calculated mean cell voltage is 14.6 volts. After work-up by molecular distillation, 19.1 g of 1-acetyl-2-methoxypyrrolidine (boiling point 53° C./0.1 mbar; $n_D^{25}=1.4674$) are obtained, which corresponds to a product yield of 76.8% and a current efficiency of 76.8%.

EXAMPLE 18

In an electrolysis cell according to the Comparative Example, there are electrolyzed 85.4 g of 1-formyl-piperidine and 241.8 g of methanol in the presence of 9.51 g of potassium tetrafluoroborate as conducting salt. After switching on the electrolysis DC the anode current density is 2 A/dm$^2$. After throughput of 2.3 Faraday per mol of 1-formylpiperidine the current is switched off. The calculated mean cell voltage is 28.8 volts. After work-up by molecular distillation, 92.8 g of 1-formyl-2-methoxypiperidine (boiling point 50° C./0.13 mbar; $n_D^{25}=1.4718$) are obtained which corresponds to a product yield of 85.9% and a current efficiency of 74.6%.

EXAMPLE 19

In an electrolysis cell as indicated in Example 4 there are electrolyzed 25.8 g of 1-acetylhexahydroazepine and 58.6 g of methanol in the presence of 2.01 g of sodium tetrafluoroborate as conducting salt. After switching on of the electrolysis DC the anode current density is 1.5 A/dm$^2$. After throughput of 2.1 Faraday/mol of 1-acetylhexahydroazepine the current is switched off. The calculated mean cell voltage is 12.3 volts. After work-up by molecular distillation, 25.7 g of 1-acetyl-2-methoxyhexahydroazepine (boiling point 53° C./0.06 mbar; $n_D^{25}=1.4775$) are obtained which corresponds to a product yield of 82.1% and a current efficiency of 78.1%.

EXAMPLE 20

In an electrolysis cell according to the Comparative Example, 96.0 g of 1-acetylpiperidine and 241.8 g of methanol are electrolyzed in the presence of 4.63 g of potassium hexafluorophosphate, 4.05 g of tetramethylammonium tetrafluoroborate and 3.43 g of tetramethylammonium nitrate as conducting salts. After switching on of the electrolysis DC the anode current density is 3 A/dm$^2$. After throughput of a current quantity of 2.0 Faraday per mol of 1-acetylpiperidine the current is switched off. The calculated mean cell voltage is 8.8 volts. After work-up by molecular distillation, 103.6 g of 1-acetyl-2-methoxypiperidine are obtained, which corresponds to a product yield of 87.3% and a current efficiency of 87.3%.

EXAMPLE 21

In an electrolysis cell made from glass and having a capacity of 80 ml, there are electrolyzed 23.5 g of 1-carbomethoxypiperidine and 52.6 g of methanol in the presence of 0.26 g of tetramethylammonium tetrafluoroborate as conducting salt. Two concentrically arranged platinum networks cylinders having 225 meshes per cm$^2$, diameters of 15 and 30 mm and a height of 50 mm are immersed in the solution as electrodes; the outer electrode serving as anode. The temperature is maintained at about 10° C. during the electrolysis. After switching on of the electrolysis DC the anode current density is 1 A/dm$^2$. After throughput of a current quantity of 2.5 Faraday per mol of 1-carbomethoxypiperidine the current is switched off. The calculated mean cell voltage is 57.0 volts. After work-up by vacuum distillation, 26.3 g of 1-carbomethoxy-2-methoxypiperidine are obtained, which corresponds to a product yield of 92.5% and a current efficiency of 73.7%.

The product yield is considerably higher than indicated in J. Am. Chem. Soc. 97 (1975), 4264–4268 with the use of tetraethylammonium tosylate as conducting salt (72%).

EXAMPLE 22

In an electrolysis cell according to Example 21, 31.3 g of 1-carbomethoxypiperidine and 70.1 g of methanol are electrolyzed in the presence of 0.73 g of tetra-n-propylammonium hexafluorophosphate. After switching on of the electrolysis DC the anode current density is 2 A/dm$^2$. After throughput of a current quantity of 2.2 Faraday per mol of 1-carbomethoxypiperidine the current is switched off. The calculated mean cell voltage is 35.1 volts. After work-up by vacuum distillation, 33.5 g of 1-carbomethoxy-2-methoxypiperidine are obtained which corresponds to a product yield of 88.4% and a current efficiency of 73.7%.

EXAMPLE 23

In an electrolysis cell according to Example 21, 31.3 g of 1-carbomethoxypiperdine and 70.1 g of methanol are electrolyzed in the presence of 2.40 g of sodium tetrafluoroborate as conducting salt. After switching on of the electrolysis DC the anode current density is 2.2 A/dm$^2$. After throughput of a current quantity of 2.5 Faraday per mol of 1-carbomethoxypiperidine the current is switched off. The calculated mean cell voltage is 16.8 volts.

After work-up by molecular distillation, 32.6 g of 1-carbomethoxy-2-methoxypiperidine are obtained, which corresponds to a product yield of 86.1% and a current efficiency of 68.8%.

EXAMPLE 24

In an electrolysis cell according to Example 21, 31.3 g of 1-carbomethoxypiperidine and 70.1 g of methanol are electrolyzed in the presence of 4.03 g of potassium hexafluorophosphate as conducting salt. After switching on of the electrolysis DC the anode current density is 2 A/dm$^2$. After throughput of a current quantity of 2 Faraday per mol of 1-carbomethoxypiperidine the current is switched off. The calculated mean cell voltage is 14.5 volts. After work-up by molecular distillation, 32.4 g of 1-carbomethoxy-2-methoxypiperidine are obtained which corresponds to a product yield of 85.5% and a current efficiency of 85.5%.

EXAMPLE 25

In an electrolysis cell according to Example 21, 31.3 g of 1-carbomethoxypiperidine and 70.1 g of methanol are electrolyzed in the presence of 0.32 g of tetramethylammonium tetrafluoroborate and 0.03 g of tetramethylammonium nitrate as conducting salt mixture. After switching on of the electrolysis DC the anode current density is 2 A/dm$^2$. After throughput of a current quantity of 2.1 Faraday per mol of 1-carbomethoxypiperidine the current is switched off. The calculated mean cell voltage is 42.8 volts. After work-up by vacuum distillation, 34.6 g of 1-carbomethoxy-2-methoxypiperidine are obtained, which corresponds to a product yield of 91.3% and a current efficiency of 87.0%.

EXAMPLE 26

In an electrolysis cell according to Example 21, 27.8 g of 1-carbomethoxypiperidine and 72.8 g of methanol are electrolyzed in the presence of 0.31 g of tetramethylammonium tetrafluoroborate as conducting salt. After switching on of the electrolysis DC the anode current density is 0.5 A/dm$^2$. After throughput of a current quantity of 5.6 Faraday per mol of 1-carbomethoxypiperidine the current is switched off. The calculated mean cell voltage is 23.7 volts. After work-up by vacuum distillation, 33.4 g of 1-carbomethoxy-2,6-dimethoxypiperidine (boiling point 62° C./0.04 mbar; $n_D^{25}=1.4582$) are obtained which corresponds to a product yield of 84.3% and a current efficiency of 60.2%.

EXAMPLE 27

In an electrolysis cell according to Example 21, 16.2 g of 1-carbomethoxypiperidine and 83.3 g of n-butanol are electrolyzed in the presence of 1.85 g of tetra-n-butylammonium tetrafluoroborate as conducting salt. After switching on of the electrolysis DC the anode current density is 1 A/dm$^2$. After throughput of a current quantity of 2.1 Faraday per mol of 1-carbomethoxypiperidine the current is switched off. The calculated mean cell voltage is 92 volts. After work-up by molecular distillation, 11.4 g of 1-carbomethoxy-2-n-butoxypiperidine ($n_D^{25}=1.4567$; boiling point 62° C./0.05 mbar) are obtained, which corresponds to a product yield of 47.3% and a current efficiency of 45.9%.

EXAMPLE 28

In an electrolysis cell made from glass according to Example 21, but with the difference that the contents of the cell are 400 ml and the height of the electrodes is 100 mm, there are electrolyzed 96.6 g of 1-carbomethoxypyrrolidine and 239.7 g of methanol in the presence of 1.2 g of tetramethylammonium tetrafluoroborate as conducting salt. After switching on of the electrolysis DC the anode current density is 3 A/dm$^2$. After throughput of a current quantity of 2.5 Faraday per mol of 1-carbomethoxypyrrolidine the current is switched off. The calculated mean cell voltage is 29.0 volts. After work-up by vacuum distillation, 110.3 g of 1-carbomethoxy-2-methoxypyrrolidine (=α-methoxy-N-carbomethoxypyrrolidine) are obtained which corresponds to a product yield of 92.6% and a current efficiency of 74.1%. The product yield is considerably higher than indicated in J. Am. Chem. Soc. 97 (1975) 4264–4268 with the use of tetraethylammonium tosylate as conducting salt (65%).

EXAMPLE 29

In an electrolysis cell according to Example 21, 29.0 g of 1-carbomethoxypyrrolidine and 78.9 g of methanol are electrolyzed in the presence of 0.36 g of tetramethylammonium tetrafluoroborate as conducting salt. After switching on of the electrolysis DC the anode current density is 3 A/dm$^2$. After throughput of a current quantity of 6.5 Faraday per mol of 1-carbomethoxypyrrolidine the current is switched off. The calculated mean cell voltage is 55.0 volts. After work-up by vacuum distillation, 32.9 g of 1-carbomethoxy-2,5-dimethoxypyrrolidine (boiling point 53.5° C./0.01 mbar; $n_D^{25}=1.4520$) are obtained, which corresponds to a product yield of 77.5% and a current efficiency of 47.7%.

EXAMPLE 30

In an electrolysis cell according to Example 21 there are electrolyzed 42.1 g of 1-carbobenzyloxypiperidine and 61.6 g of methanol in the presence of 0.31 g of tetramethylammonium tetrafluoroborate as conducting salt. After switching on of the electrolysis DC the anode current density is 2 A/dm$^2$. After throughput of a current quantity of 2.5 Faraday per mol of 1-carbobenzyloxypiperidine the current is switched off. The calculated mean cell voltage is 63.5 volts. After work-up by vacuum distillation, 42.9 g of 1-carbobenzyloxy-2-methoxypiperidine (boiling point 85° C./0.2 mbar; $n_D^{25}=1.5172$) are obtained which corresponds to a product yield of 89.6% and a current efficiency of 71.7%.

EXAMPLE 31

In an electrolysis cell according to Example 21 there are electrolyzed 20.2 g of 1-carbophenoxypiperidine and 63.9 g of methanol in the presence of 0.31 g of tetramethylammonium tetrafluoroborate as conducting salt. After switching on of the electrolysis DC the anode current density is 2 A/dm$^2$. After throughput of a current quantity of 2.5 Faraday per mol of 1-carbophenoxypiperidine the current is switched off. The calculated mean cell voltage is 23.7 volts. After work-up by vacuum distillation, 18.0 g of 1-carbophenoxy-2-methoxypiperidine (melting point 54°–55° C.) are obtained which corresponds to a product yield of 77.9% and a current efficiency of 62.3%.

EXAMPLE 32

In the same manner as in Example 5, there are electrolyzed 13.5 g of 1-(3'-trifluoromethylbenzoyl)-piperidine and 84.1 g of methanol in the presence of 0.11 g of tetramethylammonium tetrafluoroborate as conducting salt. After throughput of 2.5 Faraday per mol of 1-(3'-trifluoromethylbenzoyl)-piperidine the current is switched off. The calculated mean cell voltage is 34.1 volts. Work-up of the electrolysis solution gives 13.3 g of 1-(3'-trifluoromethylbenzoyl)-2-methoxypiperidine (boiling point 75°–80° C./0.2 mm Hg; $n_D^{25}=1.4905$) are obtained which corresponds to a product yield of 88.2% and a current efficiency of 70.6%.

EXAMPLE 33

In the same manner as in Example 5, there are electrolyzed 43.8 g of 1-benzoyl-2-methylpiperidine and 60.2 g of methanol in the presence of 0.3 g of tetramethylammonium tetrafluoroborate as conducting salt. After throughput of 2.5 Faraday per mol of 1-benzoyl-2-methylpiperidine the current is switched off. After work-up of the electrolysis solution, 39.0 g of 1-benzoyl-2-methyl-6-methoxypiperidine (boiling point 78°–81° C./0.1 mm Hg; $n_D^{25}=1.5340$) are obtained which corresponds to a product yield of 77.5% and a current efficiency of 62.0%.

BIOLOGICAL EXAMPLES

In the following Examples, the letters A and B represent the following comparative agents:

A=manganese-ethylene-1,2-bis-dithiocarbamate
B=commercial copper product (as copper chloride)

EXAMPLE I

Spring barley seeds naturally infested with Helmintho-sporium gramineum at a degree of 20% were dressed with a dressing agent containing 50% of the compounds of the invention in concentrations as indicated in Table I. The seeds were sown into bowls which subsequently were placed in a greenhouse kept cool. Later on, the plants infested with Helminthosporium gramineum and the sound plants were counted, the infection degree was evaluated and the effect of the compounds of the invention was calculated on the basis of these results (Table I).

Table I

| Compound of | Effect in % at g/dressing agent per 100 kg seeds | | | |
|---|---|---|---|---|
| Example | 300 | 200 | 100 | 50 |
| 4 | — | 100 | 100 | 95 |
| 32 | — | 100 | 95 | 60 |
| A | 75 | 60 | — | — | untreated, infested plants: 20 % infection

The results of Table I show the good effect against Helminthosporium of the mercury-free compounds of the invention and their superiority over the mercury-free comparative agent A.

EXAMPLE II

Vine plants grown from cuttings of the Muller-Thurgau variety known as being easily infested with Plasmopora were treated in their four-leaf stage with aqueous suspensions of the compound of the invention. The application concentrations were 2000, 1000 and 500 ppm of active substance. B served as comparative agent and was used in the same application concentrations as above. After drying of the sprayed layer the plants were inoculated with a suspension of zoosporangia of *Plasmopora viticola* and placed dripping wet in a moisture chamber at a temperature of 20° C. and a relative atmospheric humidity of 100%. After 24 hours, the infested plants were removed from this chamber and placed in a greenhouse having a temperature of 23° C. and an atmospheric humidity of about 80 to 90%.

After an incubation time of 7 days, the plants were moistened, placed overnight in the moisture chamber and thus the disease was incited to break out. The infection degree was expressed in % of infested leaf area as compared to untreated infested control plants, and it is indicated in Table II.

Table II

| Compound of | % Infection with Plasmopara at ppm active substance | | |
|---|---|---|---|
| Example | 2000 | 1000 | 500 |
| 33 | — | 0 | 0–3 |
| B | 5 | 10 | 20 | untreated, infested plants: 100 % infection

Table II proves the good activity against Plasmopora of the compound of the invention which is superior to that of the comparative agent.

What is claimed is:

1. A process for making an alkoxy cyclic amide which comprises anodically alkoxylating a carboxylic acid amide of the formula $$\begin{array}{c} \phantom{R^2}\diagup CH_2 \diagdown \\ R^2 \phantom{xxxx} N-C-R^1 \\ \phantom{R^2}\diagdown CH \diagup \phantom{xx} \| \\ \phantom{xxxxxx} | \phantom{xxxxx} O \\ \phantom{xxxxxx} Y' \end{array}$$

wherein:
$R^1$=hydrogen, alkyl of 1 to 8 carbons, an aryl group of 6 to 10 carbons, alkoxy of 1 to 4 carbons, benzoxy or phenoxy,
$R^2$=$C_1$ to $C_4$ alkylene and
$Y'$=hydrogen, ($C_1$–$C_4$)-alkyl or ($C_1$–$C_4$)alkoxy with a ($C_1$–$C_4$)alkanol in the presence of a conductive salt selected from the group consisting of alkali metal and tetra-($C_1$–$C_6$)alkylammonium-tetrafluoroborates, hexafluorophosphates, nitrates and mixtures thereof at a temperature of up to 100° C.

2. A process according to claim 1 wherein the quantity of electricity used is from about 2 to 5 faradays per mol of starting compound.

3. A process according to claim 1 wherein the conductive salt is selected from sodium and potassium tetrafluoroborate and hexafluorophosphate and tetramethylammonium tetrafluoroborate.

4. A process according to claim 1 wherein the concentration of the conductive salt is from about 0.01 to 2.0 mols per liter.

5. A process according to claim 1 wherein the electrolysis temperature is from about 0° to about 60° C.

6. A process according to claim 1 wherein the molar ratio of carboxylic acid amide to alkanol is about 1:1 to about 1:100.

* * * * *